United States Patent [19]

Watanabe et al.

[11] 4,390,631
[45] Jun. 28, 1983

[54] PROCESS FOR PRODUCING BACTERIA HAVING HIGH NITRILASE ACTIVITY

[75] Inventors: Ichiro Watanabe; Kanehiko Enomoto, both of Yokohama; Yasuo Ogawa, Kawasaki, all of Japan

[73] Assignee: Nitto Chemical Industry Co., Ltd., Tokyo, Japan

[21] Appl. No.: 307,268

[22] Filed: Sep. 30, 1981

[30] Foreign Application Priority Data

Sep. 30, 1980 [JP] Japan ................................ 55/135120

[51] Int. Cl.$^3$ ........................ C12N 1/38; C12P 13/02; C12N 9/78; C12N 1/20
[52] U.S. Cl. .................................... 435/244; 435/129; 435/227; 435/253
[58] Field of Search ................ 435/129, 227, 244, 253

[56] References Cited

U.S. PATENT DOCUMENTS 4,001,081  1/1977  Commeyras et al. ................ 435/129
4,248,968  2/1981  Watanabe et al. ................... 435/129

OTHER PUBLICATIONS

J. Van 'T Riet et al., Biochimica et Biophysica Acta, vol. 576, pp. 347–360, (1979).
Aoki et al., Agricultural and Biological Chemistry, vol. 45, No. 4, pp. 817–822, (1981).

Primary Examiner—Lionel M. Shapiro
Attorney, Agent, or Firm—Sughrue, Mion, Zinn, Macpeak and Seas

[57] ABSTRACT

A process is described for producing bacteria having a high nitrilase activity comprising incubating bacteria having an ability to produce nitrilase, wherein the improvement comprises using a culture medium containing a water soluble iron compound.

5 Claims, No Drawings

PROCESS FOR PRODUCING BACTERIA HAVING HIGH NITRILASE ACTIVITY

FIELD OF THE INVENTION

The present invention relates to a process for producing bacteria having a high nitrilase activity.

BACKGROUND OF THE INVENTION

In recent years, with rapid progress in the arts concerning immobilized enzymes and immobilized microbes, it has been vigorously attempted to utilize microbes or enzymes as a catalyst for various reactions.

Nitrilase has been known as an enzyme which hydrates nitriles to form corresponding amides. As typical examples of such reactions, there are descriptions that bacteria of the genus Corynebacterium and the genus Nocardia in U.S. Pat. No. 4,248,968 and bacteria of the genus Bacillus, the genus Bacteridium in the sense of Prevot, the genus Micrococcus and the genus Brevibacterium in the sense of Bergy in U.S. Pat. No. 4,001,081 have such nitrilase activity and hydrate acrylonitrile to form acrylamide.

SUMMARY OF THE INVENTION

As a result of extensive studies on a process for producing bacteria having a high nitrilase activity in a high yield for the purpose of industrially producing these enzyme sources, it has now been found that the yield of nitrilase remarkably increases when the above described bacteria are incubated using a culture medium containing a water soluble iron compound.

Thus, the present invention is a process for producing bacteria having a high nitrilase activity comprising incubating bacteria having an ability to produce nitrilase, wherein the improvement comprises using a culture medium containing a water soluble iron compound.

DETAILED DESCRIPTION OF THE INVENTION

As the bacteria used in the present invention, any bacterium may be used without regard to taxonomic classification, provided that it has an ability of hydrating acrilonitrile to form acrylamide. Preferred examples thereof include Corynebacterium strain N-771 (Deposition number in Fermentation Research Institute (FERM No. 4445), Corynebacterium strain N-774 (FERM No. 4446) and Nocardia strain N-775 (FERM No. 4447) described in the above described U.S. Pat. No. 4,248,968.

The water soluble iron compound used in the present invention is selected from inorganic and organic iron salts and organo-iron complex compounds. Examples thereof include inorganic salts such as sulfate, hydrochloride, etc., and organic salts such as acetate fumarate, etc., of divalent iron or trivalent iron, and organo-iron complex compounds composed of citric acid, tartaric acid, ethylenediaminetetraacetic acid or nitrilotriacetic acid and iron. It is particularly preferred for increasing the enzyme activity of the bacteria to use organo-iron complex compounds so that iron is present in the culture medium as an organic complex compound. An amount of these iron compounds added to the culture medium is generally at least 0.2 mg/l, preferably from 0.2 to 500 mg/l, and more preferably from 1 to 100 mg/l as iron, though the effect can be observed by addition of an amount of lower than 0.2 mg/l.

More particularly, the present invention can be carried out e.g., by incubating a strain of the above described bacteria using a culture medium comprising carbon sources such as glucose, maltose, and saccharose, e.g., nitrogen sources such as ammonia, ammonium sulfate, ammonium chloride, ammonium nitrate and urea, etc., organic nutrients such as yeast extract, meat extract, malt extract, casein hydrolysate and peptone, etc., and inorganic nutrients such as phosphric acid salts, potassium salts, magnesium salts and other metal salts, as minor nutrients, etc. To the foregoing, it is necessary to add water soluble iron compound as described above in order to increase the nitrilase activity of the bacteria. The cultivation is generally carried out at a temperature of from 25° C. to 30° C., a pH of from 5 to 8, under aerobic conditions, for from 30 to 100 hours.

The present invention is further illustrated in detail with reference to examples.

In the examples, measurement of nitrilase enzyme activity for hydrating acrylonitrile was carried out by the following method. Bacteria were separated from culture medium with a 0.05 M phosphate and washed with a 0.05 M phosphate buffer solution (pH 7.5) to obtain washed bacterial cells. Using them as an enzyme source, a suitable amount of an enzyme solution (washed cells: 1 to 5 mg) was added to 5 ml of a 0.05 M phosphate buffer solution (pH 7.5) containing 2.5% of acrylonitrile. After the above described phosphate buffer solution was added to make the total amount 10 ml, they were reacted at 10° C. for 10 minutes. Acrylamide formed in this reaction was quantitatively measured by gas chromatography, and the weight in mg (milligrams) of bacteria which formed 1μ mol per minute of acrylamide under the above described condition was valued as 1 unit.

Further, % values in the examples are by weight.

EXAMPLE 1

A basal medium (pH 7.5) comprising 1% glucose, 0.5% $(NH_4)_2SO_4$, 0.1% $KH_2PO_4$, 0.1% $MgSO_4.7H_2O$, 0.01% NaCl, 0.01% $CaCl_2.2H_2O$, 0.000004% $CuSO_4.5H_2O$, 0.00001% KI, 0.00002% $FeCl_3.6H_2O$, 0.00004% $MnSO_4.4H_2O$, 0.00002% $Na_2MoO_4.2H_2O$, 0.00004% $ZnSO_4.6H_2O$, 1% Casamino acid (produced by Difco Laboratories in U.S.A.) and 0.0002% thiamine hydrochloride was placed in medium sized test tubes in an amount of 10 ml each. To them, ferrous sulfate or ferric sulfate was added in a range of from 0 to 500 mg/l as the soluble iron, as indicated in Table 1, and the samples thus prepared were sterilized at 120° C. for 15 minutes. After cooling, sterilized $CaCO_3$ was added in an amount of 2% in order to control the pH. To them, 0.05 ml of a culture medium of Corynebacterium strain N-774 (FERM No. 4446) which was previously incubated on the above described culture medium (containing 0.001% of ferrous sulfate) was added, and cultivation was carried out with shaking at 30° C. for 3 days. After conclusion of the cultivation, the bacteria were separated by centrifugal separation and washed with a 0.05 M phosphate buffer solution (pH 7.5) to obtain washed bacterial cells. Using these washed bacterial cells, the nitrilase enzyme activity for hydrating acrylonitrile was measured. The results are as shown in Table 1.

As is clear from Table 1, in the case wherein the water soluble iron compound was not added to the basal culture medium, production of enzyme scarcely occurred, although growth of the bacteria was good. It is also clear that the enzyme activity of the bacteria greatly increases due to the presence of the water soluble iron compound, by which a large amount of enzyme was produced in the inner parts of the bacteria.

EXAMPLE 2

Basal culture medium as used in Example 1 was placed in four medium sized test tubes in amounts of 10 ml each. To them, nothing, ferrous sulfate, ferric citrate and sodium ethylenediaminetetraacetato iron complex were added, respectively, and they were sterilized at 120° C. for 15 minutes. After cooling, sterilized CaCO$_3$ was added in an amount of 2% in order to control the pH, and 0.05 ml of a culture medium of Corynebacterium strain N-774 (FERM No. 4446) used in Example 1 was added, and cultivation was carried with shaking out at 30° C. for 3 days. After conclusion of the cultivation, bacteria were separated as in Example 1, and the enzyme activity thereof was measured by the same manner as in Example 1. The results are as shown in Table 2.

As is clear from Table 2, a yield of enzyme greatly increases in the case of bacteria incubated using a culture medium to which the water soluble iron compound was added, as compared with that in the case of the bacteria incubated using the culture medium with no addition. It is understood that presence of iron ion as a state of an organic complex compound is particularly effective.

EXAMPLE 3

A culture medium (pH 7.5) comprising 1.0% glucose, 0.5% peptone, 0.3% yeast extract and 0.3% malt extract was placed in 6 test tubes in an amount of 10 ml each. Ferrous sulfate was added to 3 of them in an amount of 2 mg/l as the soluble iron, and they were sterilized at 120° C. for 15 minutes. After cooling, 0.05 ml of a culture medium of Corynebacterium strain N-774 (FERM No. 4446), Nocardia strain N-775 (FERM No. 4447), or *Brevibacterium imperiale* IAM 1654 obtained by previous incubation (using the above described culture medium to which the water soluble iron compound was not added) was added to the test tubes as indicated, and cultivation was carried out with shaking at 30° C. for 48 hours. After conclusion of the cultivation, the bacteria were separated and the enzyme activity thereof was measured in the same manner as in Example 1. The results are as shown in Table 3.

As is clear from Table 3, the bacteria incubated on the culture medium to which the water soluble iron compound was added have an increased enzyme activity as compared with the bacteria incubated using the same culture medium except without addition of a water soluble iron compound, by which a large amount of enzyme is produced in the inner parts of the bacteria.

TABLE 1

| Water soluble iron compound | | cell growth (mg/ml) | Enzyme activity (units/mg cell) |
|---|---|---|---|
| Reagent | amount added (Fe ion mg/l) | | |
| No addition (control) | | 5.29 | 0.1 |
| Ferrous sulfate | 0.05 | 4.83 | 0.2 |
| | 0.2 | 5.08 | 3.9 |
| | 0.5 | 5.16 | 25.9 |
| | 1.0 | 5.66 | 36.4 |
| | 2.0 | 5.33 | 38.7 |
| | 10 | 5.66 | 38.6 |
| | 20 | 5.82 | 43.7 |
| | 100 | 5.58 | 43.0 |
| | 200 | 5.58 | 43.1 |
| | 500 | 5.33 | 42.8 |
| Ferric sulfate | 1.0 | 5.08 | 38.4 |
| | 2.0 | 5.29 | 40.6 |
| | 10 | 5.16 | 42.2 |

TABLE 2

| | Water soluble iron compound | | |
|---|---|---|---|
| Reagent | Amount added (Fe ion mg/l) | Cell growth (mg/ml) | Enzyme activity (units/mg cell) |
| No addition (control) | | 5.29 | 0.1 |
| Ferrous sulfate | 10 | 5.66 | 38.7 |
| Ferric citrate | 11 | 5.66 | 53.3 |
| Sodium ethylenediaminetetraacetato iron complex | 16 | 5.33 | 54.4 |

TABLE 3

| Microorganism | Amount of ferrous sulfate added (Fe ion mg/l) | Cell growth (mg/ml) | Enzyme activity (units/mg cell) |
|---|---|---|---|
| Corynebacterium N-774 | 0 | 5.37 | 23.9 |
| | 2 | 5.34 | 38.2 |
| Nocardia N-775 | 0 | 4.96 | 7.8 |
| | 2 | 5.04 | 15.2 |
| *Brevibacterium imperiale* | 0 | 4.63 | 0.3 |
| | 2 | 4.54 | 1.5 |

While the invention has been described in detail and with reference to specific embodiments thereof, it will be apparent to one skilled in the art that various changes and modifications can be made therein without departing from the spirit and scope thereof.

What is claimed is:

1. A process for producing bacteria having a high nitrilase activity comprising incubating bacteria having an ability to produce nitrilase, wherein the improvement comprises using a culture medium containing a water soluble iron compound in an amount of at least 0.2 mg/l as iron.

2. A process according to claim 1, wherein said water soluble iron compound is selected from inorganic and organic iron salts and organo-iron complex compounds.

3. A process according to claim 1, wherein said water soluble iron compound is contained in the culture medium in an amount of from 0.2 to 500 mg/l of iron.

4. A process according to claim 1, wherein the incubation is carried out at pH of 5 to 8.

5. A process according to claim 1, wherein said water soluble iron compound is contained in the culture medium in an amount of from 1 to 100 mg/l of iron.

* * * * *

UNITED STATES PATENT AND TRADEMARK OFFICE
CERTIFICATE OF CORRECTION

PATENT NO. : 4,390,631
DATED : June 28, 1983
INVENTOR(S) : Ichiro Watanabe et al It is certified that error appears in the above-identified patent and that said Letters Patent is hereby corrected as shown below:

On the title page assignee should read

-- (73) Assignee: Nitto Chemical Industry Co., Ltd. & Mitsubishi Rayon Co., Ltd. --

Signed and Sealed this

Twenty-fourth Day of April 1984

[SEAL]

Attest:

GERALD J. MOSSINGHOFF

Attesting Officer

Commissioner of Patents and Trademarks